US009283049B2

(12) United States Patent
Diolaiti et al.

(10) Patent No.: US 9,283,049 B2
(45) Date of Patent: *Mar. 15, 2016

(54) CONTROL SYSTEM CONFIGURED TO COMPENSATE FOR NON-IDEAL ACTUATOR-TO-JOINT LINKAGE CHARACTERISTICS IN A MEDICAL ROBOTIC SYSTEM

(71) Applicant: Intuitive Surgical Operations, Inc., Sunnyvale, CA (US)

(72) Inventors: Nicola Diolaiti, Menlo Park, CA (US); David Q. Larkin, Menlo Park, CA (US); Thomas G. Cooper, Menlo Park, CA (US); Bruce M. Schena, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,349

(22) Filed: Sep. 5, 2014

(65) Prior Publication Data

US 2015/0057677 A1    Feb. 26, 2015

Related U.S. Application Data

(60) Continuation of application No. 13/761,439, filed on Feb. 7, 2013, now Pat. No. 8,864,752, which is a division of application No. 11/762,236, filed on Jun. 13, 2007, now Pat. No. 8,419,717.

(60) Provisional application No. 60/813,207, filed on Jun. 13, 2006.

(51) Int. Cl.
*A61B 17/00* (2006.01)
*A61B 19/00* (2006.01)
*G05B 19/19* (2006.01)

(52) U.S. Cl.
CPC ............ *A61B 19/2203* (2013.01); *G05B 19/19* (2013.01); *A61B 19/5212* (2013.01);
(Continued)

(58) Field of Classification Search
USPC ....................................................... 606/1, 130
See application file for complete search history.

(56) References Cited

U.S. PATENT DOCUMENTS 4,763,055 A    8/1988 Daggett et al.
4,864,204 A    9/1989 Daggett et al.
(Continued)

FOREIGN PATENT DOCUMENTS

EP    970663 A1    1/2000
EP    1464270 A1    10/2004
(Continued)

OTHER PUBLICATIONS

International Search Report for application No. PCT/US07/71081, Mailed on Mar. 6, 2008, 3 pages.
(Continued)

*Primary Examiner* — William Thomson
*Assistant Examiner* — Jeffrey Lipitz

(57) ABSTRACT

A medical robotic system having non-ideal actuator-to-joint linkage characteristics, includes a control system including a proximal control loop with actuator sensor feedback to control dynamic response of an actuator coupled to a distal joint which in turn, is coupled to an end effector to provide a degree of freedom movement of the end effector, a distal control loop with distal joint sensor feedback and feedforward to the actuator to ensure steady-state convergence of the distal joint position, and an end effector control loop with end-point sensor feedback to control the end effector position to reach a commanded end effector position.

15 Claims, 9 Drawing Sheets

(52) U.S. Cl.
CPC . *A61B2019/2223* (2013.01); *A61B 2019/2234* (2013.01); *A61B 2019/2242* (2013.01); *A61B 2019/2249* (2013.01); *A61B 2019/5227* (2013.01); *A61B 2019/5236* (2013.01); *A61B 2019/5238* (2013.01); *A61B 2019/5248* (2013.01); *A61B 2019/5251* (2013.01); *A61B 2019/5255* (2013.01); *A61B 2019/5259* (2013.01); *A61B 2019/5263* (2013.01); *A61B 2019/5272* (2013.01); *G05B 2219/45117* (2013.01); *Y10S 901/30* (2013.01)

(56) References Cited

U.S. PATENT DOCUMENTS

| | | | |
|---|---|---|---|
| 4,925,312 | A | 5/1990 | Onaga et al. |
| 4,987,356 | A | 1/1991 | Yamada et al. |
| 5,428,285 | A | 6/1995 | Koyama et al. |
| 5,767,648 | A | 6/1998 | Morel et al. |
| 5,792,135 | A | 8/1998 | Madhani et al. |
| 6,096,004 | A | 8/2000 | Meglan et al. |
| 6,478,028 | B1 | 11/2002 | Paolitto et al. |
| 6,692,485 | B1 | 2/2004 | Brock et al. |
| 6,817,974 | B2 | 11/2004 | Cooper et al. |
| 6,926,709 | B2 | 8/2005 | Bieger et al. |
| 8,419,717 | B2 | 4/2013 | Diolaiti et al. |
| 8,864,752 | B2 | 10/2014 | Diolaiti et al. |
| 2002/0087048 | A1 | 7/2002 | Brock et al. |
| 2003/0013949 | A1 | 1/2003 | Moll et al. |
| 2003/0169003 | A1 | 9/2003 | Cao et al. |
| 2003/0216613 | A1 | 11/2003 | Suzuki et al. |
| 2004/0093119 | A1 | 5/2004 | Gunnarsson et al. |
| 2005/0232532 | A1 | 10/2005 | Wang et al. |
| 2005/0273085 | A1 | 12/2005 | Hinman et al. |
| 2006/0108958 | A1 | 5/2006 | Brenner |
| 2006/0269387 | A1 | 11/2006 | Yamaguchi |
| 2007/0168100 | A1* | 7/2007 | Danko ................ 701/50 |
| 2007/0233044 | A1 | 10/2007 | Wallace et al. |
| 2007/0260356 | A1 | 11/2007 | Kock et al. |
| 2009/0000626 | A1 | 1/2009 | Quaid et al. |

FOREIGN PATENT DOCUMENTS

| | | |
|---|---|---|
| JP | 2002264048 A | 9/2002 |
| WO | WO-9911189 A1 | 3/1999 |
| WO | WO-2004104714 A1 | 12/2004 |
| WO | WO-2006091494 A1 | 8/2006 |

OTHER PUBLICATIONS

Letter from the Opponent of Apr. 30, 2013 Enclosed in European Office Action mailed May 14, 2013 for European Application No. 07812126.6 filed Jun. 13, 2007.

Notice of Opposition mailed May 29, 2012 for European Application No. 07812126.6 filed Jun. 13, 2007.

PCT/US07/71081 Written Opinion of the International Search Authority, mailed Mar. 6, 2008, 7 pages.

Regelungstechnik, Einführung in die Methoden und ihre Anwendung, Huthig Buch Verlag Heidelberg, Otto Follinger, 1994, pp. 270-273. (partial translation is available in EP07812126.6 opposition dated May 29, 2012 [p. 13-14]; complete translation not available.).

Scientific Bulletin of the "Petru Maior" University of Targu Mures, vol. 2 (XIX)—News Series, 2006, "Predictive Cascade Control of Electrical Drives" by Alexandru Morar, pp. 117-125, ISSN 1841-9267.

Summons to Attend Oral Proceedings mailed Apr. 8, 2014 for European Application No. 07812126.6 filed Jun. 13, 2007.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wang T. et al., "An Experimental Setup: Force Sensing and Control for Telesurgery," Proceedings of the 15th Annual International Conference of the IEEE Engineering in Medicine and Biology Society, 1993, pp. 962-963, IEEE.

Lambrechts; P. et al., "Trajectory Planning and Feedforward Design for High Performance Motion Systems", IEEE, 2004, 5, 4637-4642.

Notice of Opposition mailed Mar. 16, 2015 for European Application No. 07812126.6 filed Jun. 13, 2007, 79 pages.

Ransijin H.J.C., "Adaptive feed-forward control based on friction identifcation for the Stäubli RX90 robot Confidential," University of Twente, 2005, chapter 5, 16 pages.

Ransijin H.J.C., "Adaptive feed-forward control based on friction identification for the Stäubli RX90 robot," University of Twente, Faculty of Engineering Technology, Laboratory of Mechanical automation, Master Thesis, Jul. 2005, 138 pages.

* cited by examiner

CONTROL SYSTEM CONFIGURED TO COMPENSATE FOR NON-IDEAL ACTUATOR-TO-JOINT LINKAGE CHARACTERISTICS IN A MEDICAL ROBOTIC SYSTEM

CROSS REFERENCE TO RELATED APPLICATIONS

This application is a continuation of U.S. application Ser. No. 13/761,439 filed Feb. 7, 2013, which is a division of U.S. application Ser. No. 11/762,236 filed Jun. 13, 2007, now U.S. Pat. No. 8,419,717, which claims priority to U.S. Provisional Application No. 60/813,207 filed Jun. 13, 2006, each of which is incorporated herein by reference.

FIELD OF THE INVENTION

The present invention generally relates to medical robotic systems and in particular, to a control system configured to compensate for non-ideal actuator-to-joint linkage characteristics in a medical robotic system.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for medical robotic systems used for performing such minimally invasive surgical procedures is strong and growing.

Examples of medical robotic systems include the daVinci® Surgical System and the daVinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist™ articulating surgical instruments or tools, which are modeled after the human wrist so that when added to the motions of the robotic arm assembly holding the surgical instrument or tool, they allow at least a full six degrees of freedom of motion, which is comparable to or even greater than the natural motions of open surgery.

In such a system, a patient-side cart typically has three or more robotic arm assemblies each having a slave manipulator for holding and manipulating a medical device such as a surgical tool or image capturing device for performing or viewing a medical procedure at a surgical site within a patient. To manipulate these medical devices, the surgeon's console also includes master manipulators which may be selectively associated with the slave manipulators holding them. Typically, two such master manipulators are provided, one for each hand of the operating surgeon.

Precise control in the positioning and manipulation of the surgical tools and their end effectors is important for performing successful medical procedures on patients. Linkages coupling joint actuators to driven joints of the surgical tools or their manipulators are generally fairly rigid so that surgical tool positions and velocities, and in particular, those of their end effectors, may be reasonably and quickly estimated in such medical robotic systems by applying kinematic transforms to sensed positions, velocities, accelerations, or torques of the actuators. However, when linkages are characterized by non-idealities such as cable friction, hysteresis and compliance, tool positions determined by applying kinematic transforms to sensed positions, velocities, accelerations, or torques of the actuators may result in excessive estimation errors in the end effector positions and consequently, diminished control capability for a surgeon performing a medical procedure.

Furthermore, the compliance and friction of the cable transmission affect the way the torques propagate from motors to the end effectors of the surgical tools. The capability of performing surgical procedures or gestures that require a fine control over the forces and torques applied by the end effectors of the surgical tools on the manipulated tissues or objects (e.g. suturing), is thus diminished.

OBJECTS AND SUMMARY OF THE INVENTION

Accordingly, one object of one or more aspects of the present invention is a control system with accurate position control of surgical tools and/or their end effectors in the presence of non-negligible non-idealities in linkages coupling their associated actuators to their driven joints.

This and additional objects are accomplished by the various aspects of the present invention as summarized by the claims that follow below.

Another aspect is a method for controlling movement of an end effector of a medical device, comprising: generating a distal joint command using an end effector command and a state of the end effector; generating an actuator command using the distal joint command and a state of a distal joint mechanically coupled to the end effector so as to be capable of moving the end effector; generating an actuator feedback using the actuator command and a state of an actuator mechanically coupled to the distal joint so as to be capable of moving the distal joint; and providing the actuator feedback to the actuator so as to cause corresponding movements of the states of the actuator, the distal joint, and the end effector.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
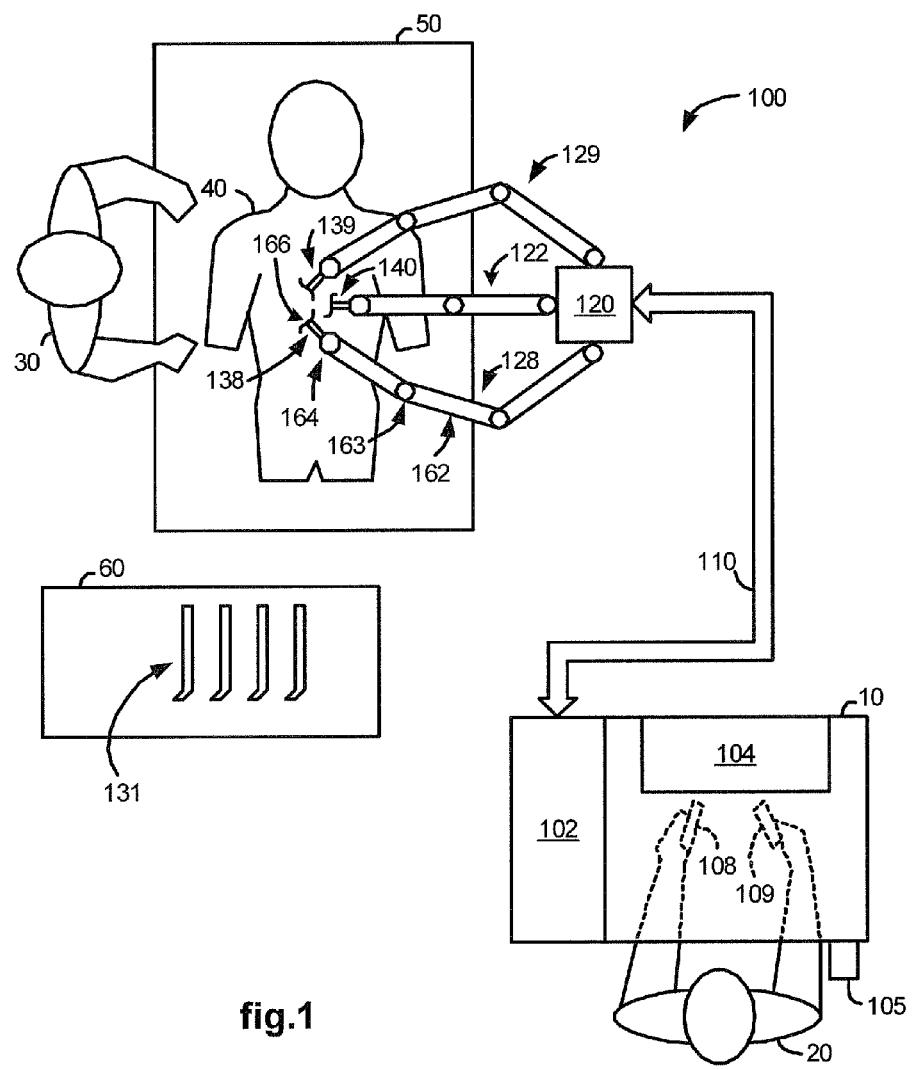
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 utilized by a Surgeon 20 while performing a medical procedure, such as a diagnostic or surgical procedure, with assistance from one or more Assistants 30, on a Patient 40 who is lying down on an operating table 50.

Figure 2:
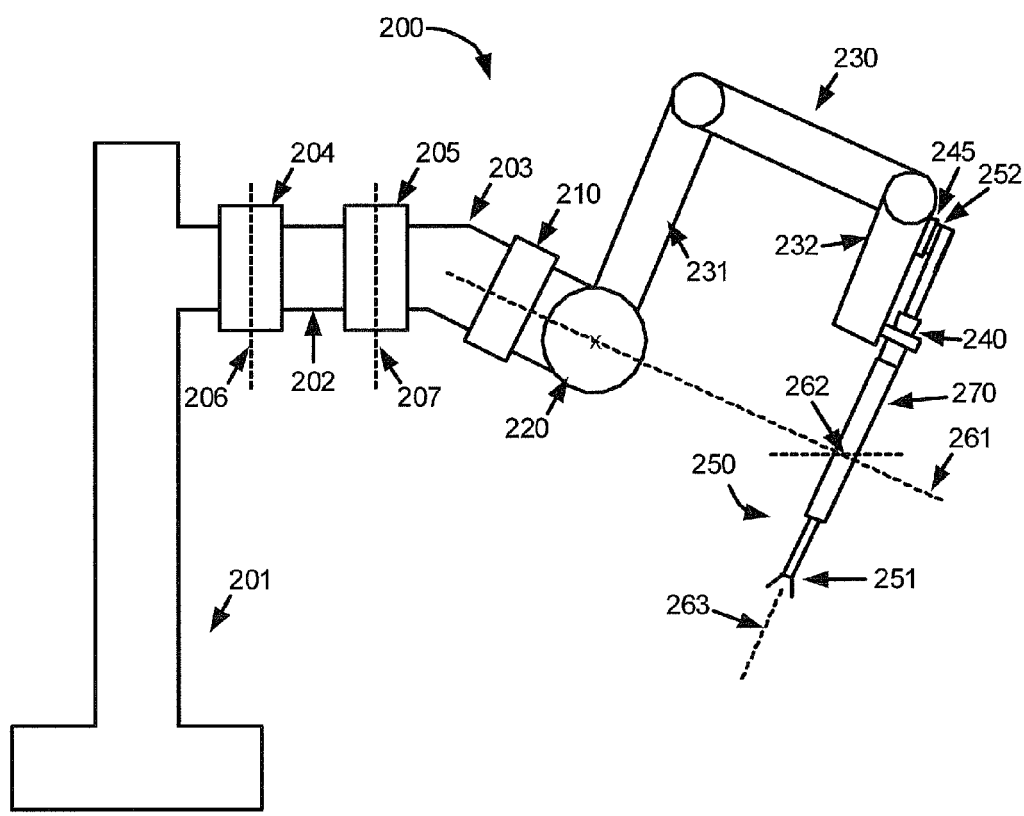
FIG. 2 illustrates a side view of a simplified robotic arm assembly holding a surgical tool which may be manipulated by an input device through a control system utilizing aspects of the present invention.

In this system, each medical device is shown to have its own associated robotic arm assembly for holding and manipulating the medical device (such as shown in FIG. 2), and its own associated incision for entry into the Patient 40 for performing the medical procedure. In particular, each of the surgical tools 138, 139, as well as an image capturing device such as a stereoscopic endoscope 140, is conventionally inserted through a tool guide, trocar or cannula into the Patient 40 so as to extend down to the surgical site through its corresponding minimally invasive incision, such as incision 166 for the tool 138.

The number of medical devices used at one time and consequently, the number of robotic arms being used in the system 100 will generally depend on the medical procedure being performed and the space constraints within the operating room, among other factors. If it is necessary to change a tool being used during a procedure, the Assistant 30 may remove the tool no longer being used from its robotic arm assembly and replace it with another tool 131 from a tray 60 in the operating room.

Figure 3:
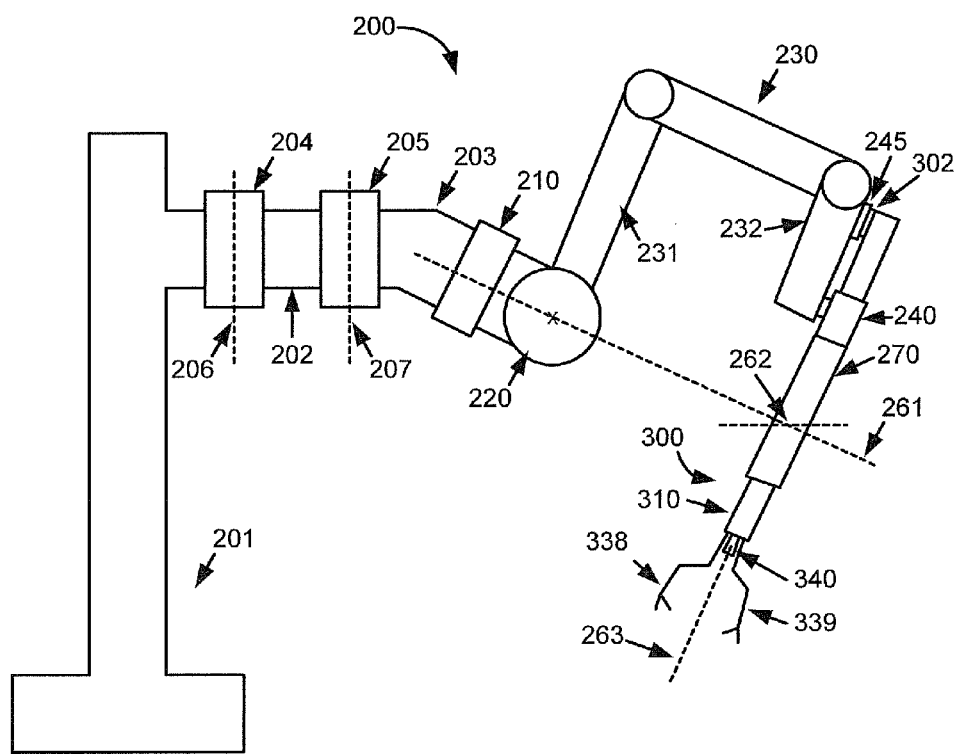
FIG. 3 illustrates a side view of a simplified robotic arm assembly holding a single-port entry bundled unit of medical devices which may be manipulated by input devices through control systems utilizing aspects of the present invention.
Figure 4:
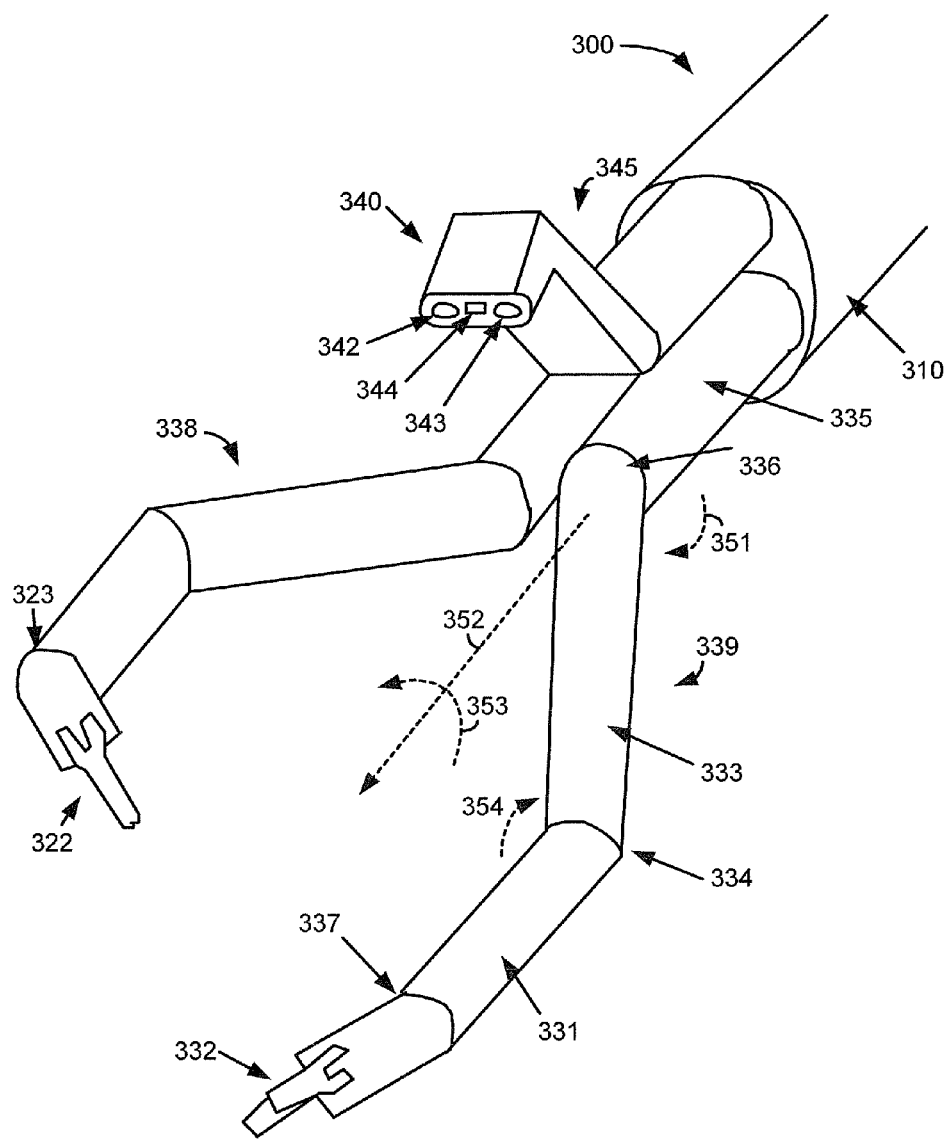
FIG. 4 illustrates a perspective view of a distal end of a simplified single-port entry bundled unit of medical devices which may be manipulated by input devices through control systems utilizing aspects of the present invention.

When the medical robotic system includes a single-port entry device with surgical tools and an image capturing device such as shown in FIG. 4, however, only one robotic arm assembly (such as shown in FIG. 3) and only one port into the Patient 40 may be necessary to perform a medical procedure. The port in this case may be an incision such as incision 166 or a natural body orifice through which the single-port entry device may be robotically moved to a surgical site or workspace in the patient. In such a case, the control system and sensory architecture described herein in reference to FIGS. 5-11 are also applicable, but with the surgical tools 138, 139 and camera 140 understood as being held by only one robotic arm assembly such as robotic arm assembly 128, or other appropriate driving mechanism.

The console 10 includes a 3-D monitor 104 for displaying a 3-D image of a surgical site to the Surgeon, left and right manipulatable control devices 108, 109 (also referred to herein as "master manipulators" or "input devices"), a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the console 10 or positioned next or near to it, or it may comprise a number of processing or controller components that are distributed in a distributed processing fashion throughout the system 100.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

The Surgeon performs a medical procedure by manipulating the control devices 108, 109 so that the processor 102 causes corresponding movement of their respectively associated surgical tools 138, 139, while the Surgeon views the surgical site in 3-D on the console monitor 104 as it is captured by the stereoscopic endoscope 140.

Preferably, control devices 108, 109 will be provided with at least the same degrees of freedom as their associated tools 138, 139 to provide the Surgeon with telepresence, or the perception that the control devices 108, 109 are integral with the tools 138, 139 so that the Surgeon has a strong sense of directly controlling the tools 138, 139. To this end, position, velocity, acceleration, force, and tactile feedback sensors may be employed on the tools 138, 139 to transmit position, velocity, acceleration, force, and tactile sensations from the tools 138, 139 back to the Surgeon's hands as he/she operates the control devices 108, 109.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

In addition, the real-time image is preferably projected into a perspective image such that the Surgeon can manipulate the end effectors of the tools 138, 139 through their corresponding control devices 108, 109 as if viewing the workspace in substantially true presence. By true presence, it is meant that the presentation of an image is a true perspective image simulating the viewpoint of an operator that is physically manipulating the tools 138, 139. Thus, the processor 102 transforms the coordinates of the tools 138, 139 to a perceived position so that the perspective image is the image that one would see if the endoscope 140 was located directly behind the tools 138, 139.

The processor 102 performs various functions in the system 100. One important function that it performs is to translate and transfer the mechanical motion of control devices 108, 109 to their respective slave manipulator(s) through control signals over bus 110 so that the Surgeon can effectively manipulate the tools 138, 139. Another important function is to implement various control system and/or controller processes as described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system such as in printed circuit boards installed in the patient side cart 120 and slave manipulators of the robotic arm assemblies 128, 129, 122, as well as, or alternatively to, the console 10.

For additional details on the construction and operation of various aspects of a medical robotic system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

FIG. 2 illustrates, as an example, a side view of a simplified (not necessarily in proportion or complete) robotic arm assembly 200 (which is representative of the robotic arm assemblies 128, 129) holding a surgical tool 250 (which is representative of tools 138, 139) for performing a medical procedure. A tool guide 270 is inserted through a minimally invasive incision in a patient, and coupled to the robotic arm assembly 200 by a guide holder 240. The surgical tool 250 may then be inserted into the patient through the tool guide 270. The robotic arm assembly 200 is mechanically supported by a base 201, which may be part of a patient-side movable cart or affixed to the operating table or ceiling.

Links 202, 203 are coupled together and to the base 201 through horizontal setup joints 204, 205. The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or less of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes two active joints and a number of gears driven by motors. A yaw joint 210 allows arm section 230 to rotate around an axis 261, and a pitch joint 220 allows arm section 230 to rotate about an axis perpendicular to that of axis 261 and orthogonal to the plane of the drawing.

The arm section 230 is configured so that sections 231, 232 are always parallel to each other as the pitch joint 220 is rotated by its motor. As a consequence, the instrument 250 may be controllably moved by driving the yaw and pitch motors so as to pivot about the pivot point 262, which is generally located through manual positioning of the setup joints 204, 205 so as to be at the point of entry into the patient. In addition, the surgical tool 250 is coupled to a carriage 245 on the arm section 230 which in turn is coupled to a linear drive mechanism to extend or retract the tool 250 along its insertion axis 263. An interface 252, which includes mating parts of the motor driven gears on the carriage 245 and a proximal end of the tool 250, facilitates driving wrist joints and other drivable members of an end effector 251 of the tool 250 using conventional gear, pulley and cable arrangements, as well as facilitating rotation of a shaft of the tool 250 so as to provide roll angular movement of the tool 250 about its insertion axis 263.

Figure 5:
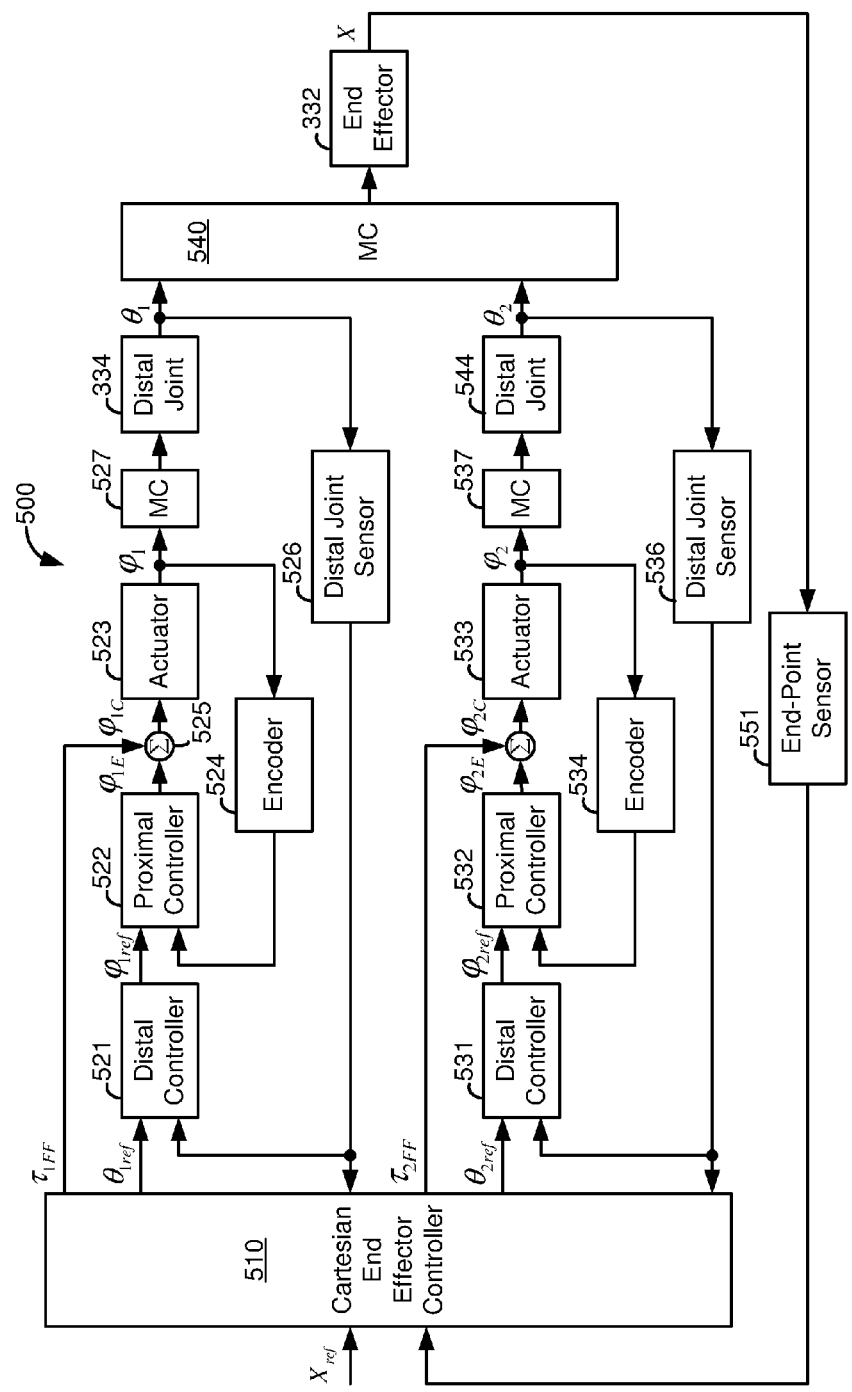
FIG. 5 illustrates a block diagram of a control system for a medical robotic system, utilizing aspects of the present invention.

Although each of the yaw joint 210, pitch joint 220 and motor driven gears in the carriage 245 is controlled by an individual joint or gear controller, the controllers may be controlled by a common master/slave control system such as shown in FIG. 5, so that the tool 250 may be controlled through user (e.g., surgeon or operator) manipulation of its associated control device.

FIG. 3 illustrates, as an example, a simplified side view of the robotic arm assembly 200 adapted this time to hold and manipulate a single-port entry device 300, and FIG. 4 illustrates, as an example, a perspective view of a distal end of the single-port entry device 300. The single-port entry device 300 includes removable surgical tools 338, 339 for performing a medical procedure and a removable image capturing unit 340 for viewing the procedure at a surgical site within a patient. Each of the tools 338, 339 and image capturing unit 340 extends through a separate lumen formed in an inner core of the single-port device 300. Replacement of one or both of the surgical tools 338, 339 during or in preparation for performing a medical procedure may then be accomplished by removing the tool that is no longer needed from its lumen and replacing it with a substitute tool by inserting the substitute tool in the vacated lumen. Alternatively, if unused lumens are available, an additional tool may be inserted through one of those available lumens without removing any other tools already in place.

The image capturing unit 340 preferably includes a stereoscopic pair of cameras 342, 343 for three-dimensional imaging of the surgical site and an illuminating device 344 such as a light emitting diode (LED) or a fiber optics bundle carrying light from an external source, to enhance visibility of objects in the captured images. Auxiliary image capturing units, such as an ultrasound probe, may also be provided in available lumens of the single-port entry device 300 for "seeing" into anatomic structures for surgical or diagnostic purposes.

In some embodiments, an overtube 310 is also included in the single-port device 300 for protecting its inner core and the medical devices (i.e., surgical tools and image capturing units) inserted therethrough. The overtube 310 may be rigid. Alternatively, it may be formed of flexible material or comprise actively and/or passively bendable sections so that the single-port device 300 may conform to the shapes of body lumens as it moves therethrough to a surgical site within a patient.

The single-port device 300 is inserted into the tool guide 270 which is coupled to the guide holder 240 of the robotic arm assembly 200. As previously described in reference to FIG. 2, movement of the robotic arm assembly 200 causes the tool guide 270 and the single-port device 300 inserted therein, to pivot about the pivot point 262 which is preferably the point of insertion of the tool guide 270 into the patient body. The insertion point may be a minimally invasive surgical incision or a natural body orifice connected to a body lumen leading to a surgical site within the patient.

An interface 302 comprising mating parts on the carriage 245 and the proximal end of the single-port device 300 such as motor driven gears that actuate movement of the surgical tools 338, 339 and image capturing unit 340 through conventional joints, cable and pulley systems. The surgical tools 338, 339 are equipped with end effectors 322, 332 that are configured with wrist mechanisms 323, 337 that allow the end effectors 322, 332 to be oriented in various poses. The surgical tools 338, 339 are also equipped with controllably extendable and bendable arms that facilitate positional and orientational movement of the end effectors 322, 332. To facilitate their controlled bending, bend sensors may be employed in the arms. Joint sensors may also be employed for determining end effector positions based upon kinematic calculations.

As shown in FIG. 4, the surgical tools 338, 339 each have a controllably extendable, rotatable, and bendable arm to which their respective end effectors 322, 332 are coupled to by wrist mechanisms 323, 337. For example, the arm of the surgical tool 339 comprises three links 331, 333, 335 coupled by distal joints 334, 336. The proximal link 335 is controllably extendable and retractable along an insertion axis 352 (which is preferably parallel to the insertion axis 263 of the single-port device 300), and is controllably rotatable (as shown by rotation angle 353) about the insertion axis 352. The middle link 333, on the other hand, is controllably bendable by distal joint 336 relative to the link 335 (as shown by bend angle 351), and the distal link 331 is coupled to the links 333, 335 and bendable by distal joint 334 so that its bend angle 354 is in an opposite direction as that of the link 333 and consequently, keeps links 331, 335 in parallel alignment.

The arm of the surgical tool 338 is similarly constructed as that of the surgical tool 339. Additional details for one example of the wrist mechanisms 323, 337 are provided in commonly owned U.S. Pat. No. 6,817,974 "Surgical Tool Having Positively Positionable Tendon-Actuated Multi-Disk Wrist Joint," which is incorporated herein by this reference.

The image capturing unit 340 also has a controllably extendable, rotatable, and bendable arm 345 that facilitates at least insertion/retraction of the image capturing unit 340 along its insertion axis (which may be parallel to the insertion axis 263 of the single-port device 300) and pitch motion in order to achieve a sufficient elevation of the image capturing device 340 "above" the surgical tools 338, 339 so as to properly view them during a surgical procedure. Additional degrees of freedom, such as roll angular movement of the image capturing device 340 about its insertion axis, may also be provided in order to facilitate additional positioning and orientation capabilities for the image capturing device 340. For enhanced maneuverability, the image capturing arm 345 may also be bendable such as the controllably bendable, rotatable, and extendable arms of the surgical tools 338, 339.

Figure 6:
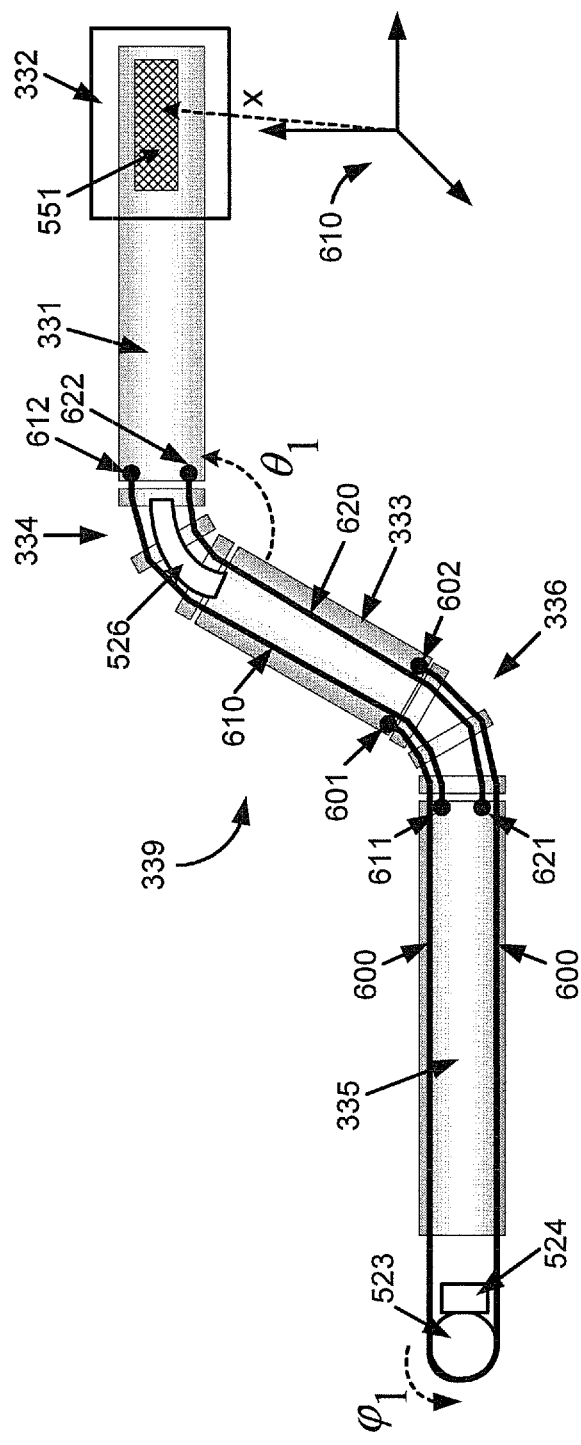
FIG. 6 illustrates a side view of a simplified surgical tool with articulatable elbows suitable for insertion in a single-port entry bundled unit of medical devices for use with a medical robotic system utilizing aspects of the present invention.

FIG. 5 illustrates, as an example, a block diagram of a control system 500 used for controlling the end effector 332 of the surgical tool 339, and FIG. 6 illustrates, as an example, a side view of a simplified depiction of the surgical tool 339. Although certain types of sensors are described as being used in the following description of the control system 500, it is to be appreciated that the described sensors shall not be limiting. In particular, various types of sensors may be used and are fully contemplated to be within the scope of the present invention, such as those shown and described in reference to FIGS. 7 and 8. Accordingly, it is to be understood that any type of sensor (or combinations thereof) that senses any aspect of the state of a controlled element over time, such as its position (either linear or angular), velocity, acceleration, orientation, and/or forces and torques exerted by it or against it may be used in alternative embodiments of the control system 500.

Note that the surgical tool 339 depicted in FIG. 6 is preferably utilized in minimally invasive surgical devices having several distal articulations that are characterized by non-negligible compliance and hysteresis characteristics in cable transmissions actuating the tool mechanism. For example, the tool 339 may be used in a single-port entry device since the additional distal degrees of freedom provided by its articulatable elbows (e.g., distal joints 334, 336 for the tool 339) serve to help compensate for the lack of independent robotic arm assemblies for each of the surgical tools 338, 339. As another example, it may be used as, or as a part of, a flexible articulated device (e.g. with an actively controlled flexible entry guide) whose shape is controlled in order to minimize its contact with soft tissue of the Patient, as well as manipulation of its end effector 332 for performing a medical procedure on the Patient.

Referring first to FIG. 6, the surgical tool 339 includes three basic components: an actuator 523, the distal joint 334 and the end effector 332. The actuator 523 is preferably a motor which has a rotor driving a cable (or system of cables) connected to the distal joint 334 so as to controllably bend the distal joint 334. It is able to do this, because the distal joint 334 is coupled to the distal joint 336 (which in turn, is coupled to the actuator 523) so as to move with it, but in an opposite rotation as shown in FIG. 4, using a multiple cable scheme as depicted therein. As an example, a primary or actuation cable 600 is wrapped around a rotor of the actuator 523. The ends of the primary cable 600 extend through a hollow of the proximal arm link 335, and are tied to opposing points 601, 602 on an inner wall of a proximal end of the middle arm link 333. When the rotator rotates, it causes the primary cable 600 to be pulled in one direction or another (depending upon the direction of the rotation) and the distal joint 336 to bend in the direction of the pull. Secondary or constraint cables 610, 620, on the other hand, are not directly connected to any actuator, but extend through a hollow of the middle arm link 333, and have proximal ends tied to opposing points 611, 621 of an inner wall of the proximal arm link 335 and distal ends tied to opposing points 612, 622 of an inner wall of the distal arm link 331, so that when the actuator 523 causes the distal joint 336 to bend in one direction (by causing the primary cable 600 to be pulled in that direction), the secondary cables 610, 620 cause the distal joint 334 to bend in a substantially equal, but opposite direction.

The distal joint 334, in turn, is connected to the end effector 332 so that bending of the distal joint 334 results in movement of the end effector 332. In this example, an encoder 524 is coupled to the actuator 523 to sense the rotation angle $\phi_1$ of its rotor, a distal joint sensor 526 is positioned proximate to or within the distal joint 334 to sense its bend angle $\phi_1$, and an end-point sensor 551 is mounted on or proximate to the end effector 332 so as to sense its position in a reference frame 610. Examples of the encoder 524, distal joint sensor 526, and end-point sensor 551 are described below in reference to FIG. 8. Note that the encoder 524 can be replaced by any other type of local sensor that is appropriate to close a local feedback loop to control the actuator 523 in order to achieve its desired state.

Referring now to FIG. 5, the control of two distal joints 334, 544 is depicted therein, each joint controlling one degree of freedom movement of the end effector 332. As shown in FIG. 4, the coupled movement of the distal joints 334, 336 controls bending of a middle arm link 333 of the end effector 332 relative to the proximal arm link 335. The distal joint 544, on the other hand, may control rotation of the proximal arm link 335 about the insertion axis 352. Additional distal joints and corresponding joint control loops may also be added to the control system 500, such as, for example, controlling the insertion/retraction of the proximal arm link 335 along the insertion axis 352, or controlling any of the wrist joints of the wrist mechanism 337.

A Cartesian end effector controller 510 receives an end effector command $X_{ref}$ and information generated by an end-point sensor 551 of a position "X" of the end effector 332. The Cartesian end effector controller 510 generates, through inverse kinematics computations, first and second distal joint commands $\theta_{1ref}$, $\theta_{2ref}$ using the two inputs. The end effector command $X_{ref}$ is received from one of the control devices 108, 109 associated with the end effector 332 and typically represents an operator manipulated displacement of the control device in its frame of reference. The end-point sensor 551 is typically mounted on, or otherwise proximate to, the end effector 332, so as to provide information from which its position X, and its orientation, may be determined.

The Cartesian end effector controller 510 translates the end effector command $X_{ref}$ into the reference frame of the end effector position X and computes an end effector position error $X_{ERR}$ as a difference between the translated end effector command $X_{ref}$ and the end effector position X. Alternatively, both the end effector command $X_{ref}$ and the end effector position X may be translated to a common reference frame such as a camera reference frame, a surgeon eye reference frame, or a world reference frame that remains fixed throughout the medical procedure. The end effector position error $X_{ERR}$ is then translated into first and second distal joint commands $\theta_{1ref}$, $\theta_{2ref}$, using conventional transform techniques.

A distal controller 521 receives the distal joint command $\theta_{1ref}$ from the Cartesian end effector controller 510 and information of a distal joint bend angle $\theta_1$ sensed by the distal joint sensor 526, computes a distal joint position error $\theta_{1ERR}$ as a difference between the two, and translates the error into an actuator command $\phi_{1ref}$. In a similar manner, a proximal controller 522 receives the actuator command $\phi_{1ref}$ from the distal controller 521 and information of an actuator position $\phi_1$ sensed by the encoder 524, computes an actuator position error $\phi_{1ERR}$ as a difference between the two, and translates the error into an actuator feedback error $\phi_{1E}$ which is provided through a summing node 525 to the actuator 523.

Due to the compliance, friction, backlash and hysteresis experienced by a mechanical coupling (MC) 527 such as a cable (or other linkage) that mechanically couples the actuator 523 to the distal joint 334, the Cartesian end effector controller 510 preferably also computes a feed-forward torque command $\tau_{1FF}$ to compensate for such transmission non-idealities and provides it to the summing node 525 so that it is summed with the actuator feedback error command $\phi_{1E}$ to generate a compensated actuator command $\phi_{1C}$. The compensated actuator command $\phi_{1C}$ is then provided to the actuator 523 to ensure that a target steady-state condition for the distal joint bend angle $\theta_1$ converges to its commanded position $\theta_{1ref}$ during the control process. The feed-forward torque command $\tau_{1FF}$ in this case is calculated using appropriate friction and compliance models for the cable so as to compensate for its non-idealities. Without the feed-forward torque command $\tau_{1FF}$, the distal joint bend angle $\theta_1$ may have difficulty converging to its target steady-state commanded value, even though the actuator position error $\phi_{1ERR}$ is zeroed by the inner control loop controlled by the proximal controller 522.

Movement of the distal joint 334 thereupon causes corresponding movement of the end effector 332 through a mechanical coupling (MC) 540 that couples the two. Control of the second distal joint 544 (and any other distal joints controlling other degrees of freedom movement of the end effector 332) is performed in the same manner as described in reference to the control of the first distal joint 334 above.

A key feature of the control system 500 is its use of multiple control loops. In an inner loop, the proximal controller 522 zeroes the actuator position error $\phi_{1ERR}$. This inner loop is a relatively high-speed loop that tightly controls the dynamic performance of the control system 500. In a middle loop, the distal controller 521 zeroes the distal joint position error $\theta_{1ERR}$. This middle loop is generally slower performing than the inner loop, because the distal joint sensor 526 is generally slower and has lower resolution than the encoder 524. However, because of the relative slow motion of the Surgeon's hands (typically in the range of 0 to 15 Hz) compared to the bandwidth of the inner control loop, the distal joint sensor 526 is capable of providing additional compensation for non-ideal actuator-to-joint linkage characteristics in the range of frequencies that are important to surgical applications. Addition of the feed-forward torque command TIFF allows the distal controller 521 to ensure steady-state convergence to its target value for the distal joint angle $\theta_1$ and consequently the end effector position X. Finally, in the outermost loop, the end effector controller 510 zeroes the end effector position error $X_{ERR}$ and in so doing provides more refined compensation of the cable non-idealities.

The control system 500 may be used in applications where it is desirable to achieve, besides fine position control, a refined control of the interaction forces and torques between the end effector 332 of the surgical tool 339 and the patient tissues or manipulated objects (e.g. when suturing). Indeed the combination of local sensing at the actuator 523, distal joint position sensing at the distal joint 334, and end point sensing at the end effector 332 provides information of the overall hysteresis and compliance of the cable transmission from which the Cartesian end effector controller 510 is able to estimate the cable tension and therefore to adjust the actuator command $\phi_{1ref}$ in such a way that the interaction forces and torques at the end effector can be controlled with better accuracy than in the case of a simple local loop closed around the actuator 523.

Also, in this example, the direct knowledge of distal joint angles $\theta_1$, $\theta_2$ allows the Cartesian end effector controller 510 to accurately compute the Jacobian matrix for the direct and inverse kinematic transforms used to convert the end effector position error $X_{ERR}$ to first and second distal joint commands $\theta_{1ref}$, $\theta_{1ref}$. In highly miniaturized surgical devices, however, direct joint position measurements may not be available because of size constraints. In that case, only end-point sensing may be available and the joint angles $\theta_1$, $\theta_2$ may not be known with accuracy because of non-idealities in the cable transmission. Thus, in this case, inaccuracies may occur in the kinematic transformations from the Cartesian set-point $X_{ref}$ to the end effector position X due to the absence of reliable position information for the joints. In such case, joint models may be employed along with actuator position and torque sensors to estimate the distal joint positions $\theta_1$, $\theta_2$ for use in the control system 500 as substitutes for the distal joint sensors 526, 536. To improve the accuracy of the model, the model may be updated using information sensed by a joint contact, proximity, force, or other type of sensor that may be too slow for direct feedback purposes (unlike the distal joint sensors 526, 536), but accurate enough for updating the joint models. Note, however, that if the end effector 332 is attached to fully actuated, non-redundant, six degrees-of-freedom ("6 DOF") slave manipulator, a 6 DOF sensor on the tip of the end effector 332 may provide sufficient information to uniquely determine the distal joint angles by means of inverse kinematics transforms. In this case, the tip sensor information, combined with the encoder measurements and forward kinematics transforms, directly relates to the current amount of "stretch" or "slop" in the cable transmission and may be used to generate refined actuator commands.

Figure 7:
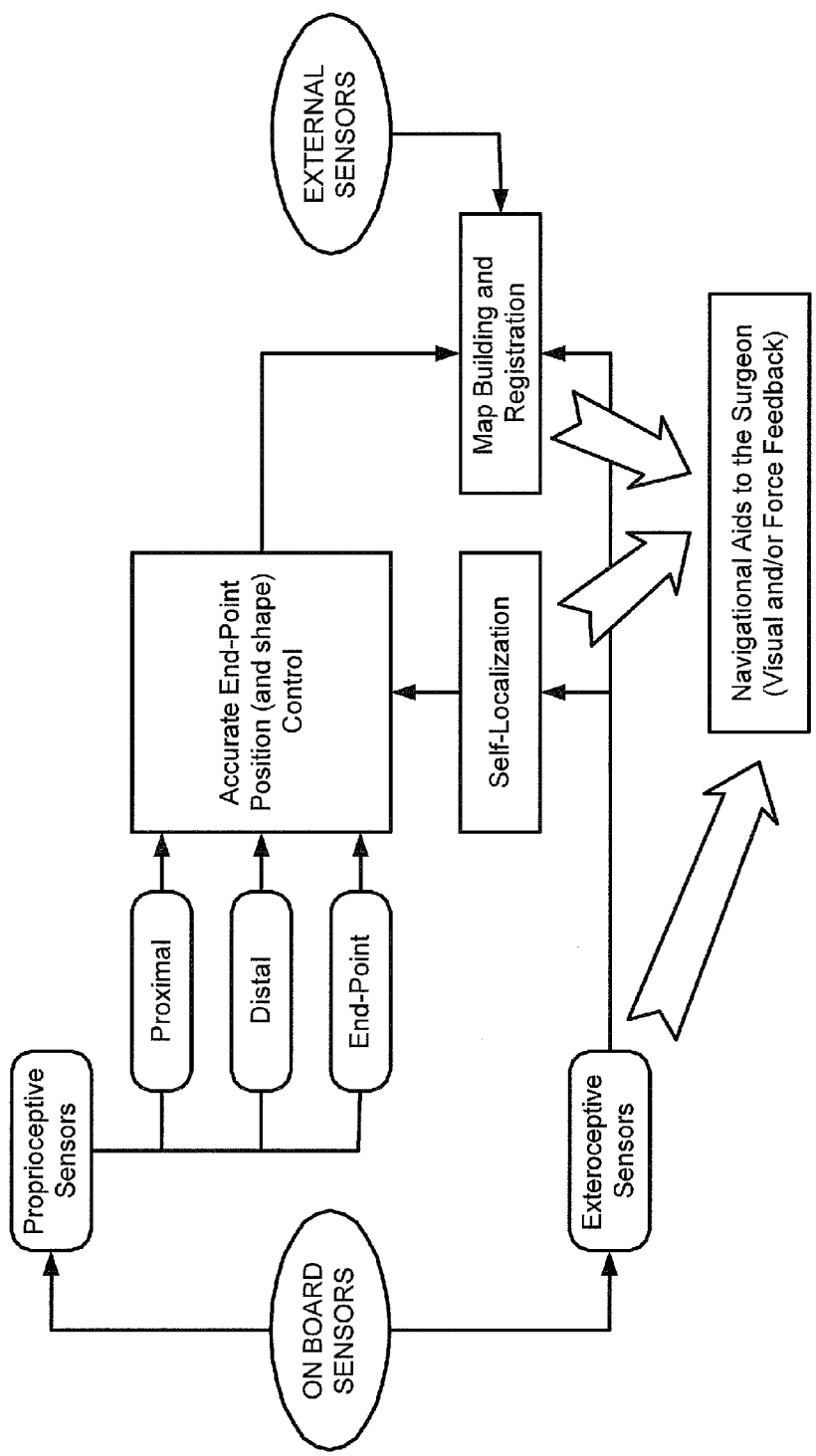
FIG. 7 illustrates a schematic diagram of a sensory architecture for a medical robotic system utilizing aspects of the present invention.

FIG. 7 illustrates, as an example, a schematic diagram of a sensory architecture for constructing a map of the Patient's anatomy and providing navigational aids to help the Surgeon navigate the single-port entry device 300 (or other medical device) along complex body structures to a surgical site within the Patient using the medical robotic system 100.

Besides information provided by proprioceptive sensors such as those used in the control system 500 for position control, information provided by exteroceptive sensors mounted on or in adjacent lumens to the surgical tools 338, 339, such as force and ultrasound sensors, along with information provided by external sensors, can be utilized to locate the single-port entry device 300 in an absolute reference frame and with respect to the Patient's anatomy. Registration with pre-operative imaging can also be used to compute virtual fixtures as navigational aids that allow the Surgeon to avoid contact with delicate organs or blood vessels of the Patient.

The relative position of the surgical tools 338, 339 with respect to the surrounding environment is used to further refine their respective end effector position and distal joint bending control. Together, map-building, self-localization, and exteroceptive sensors may be used to provide haptic and visual aids to the Surgeon in order to help navigate through the Patient's complex anatomical structures.

Sensor fusion techniques may be used to combine information from different sources for control, localization, map building, and navigational purposes. Since each sensor is characterized by its own noise levels, accuracy, and bandwidth, it is likely that at any given time a certain level of contradiction or inconsistency exists between information being provided by different sensors. Probabilistic algorithms may be used to overcome this problem and to reduce the impact of outliers on the map-building and localization processes involved with conventional Simultaneous Localization and Map Building (SLAM) techniques. In particular, Bayesian techniques and Extended Kalman Filters (EKF) provide the theoretical foundations to the successful implementation of the scheme depicted in FIG. 7. As an example of using such Bayesian techniques, see commonly owned U.S. patent application Ser. No. 11/130,471 entitled "Method and System for Performing Tool Tracking during Minimally Invasive Robotic Surgery," filed May 16, 2005, which is incorporated herein by this reference.

Figure 9:
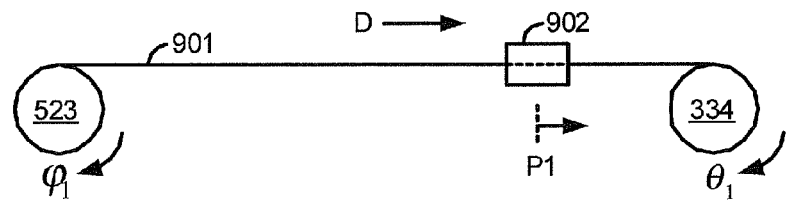
FIG. 9 illustrates a first embodiment of a linear displacement sensor for use with a control system utilizing aspects of the present invention.

A significant advantage of using sensor fusion in a global data structure such as shown in FIG. 9 is that the sensory architecture is intrinsically modular. For example, the Surgeon might use an ultrasonic sensor at one point of a medical procedure and replace it at a later time during the procedure with a force sensor in order to determine a more accurate and complete model of the tissue of interest. To enable this type of flexibility, a specific sensor model may be associated to each sensorized instrument. Once such models are available, the sensor-fusion architecture allows the number and type of sensors used to be changed during a medical procedure (i.e., inter-operatively) while retaining a consistent and unified sensory architecture for control, self-localization, map building, and navigational purposes.

Figure 8:
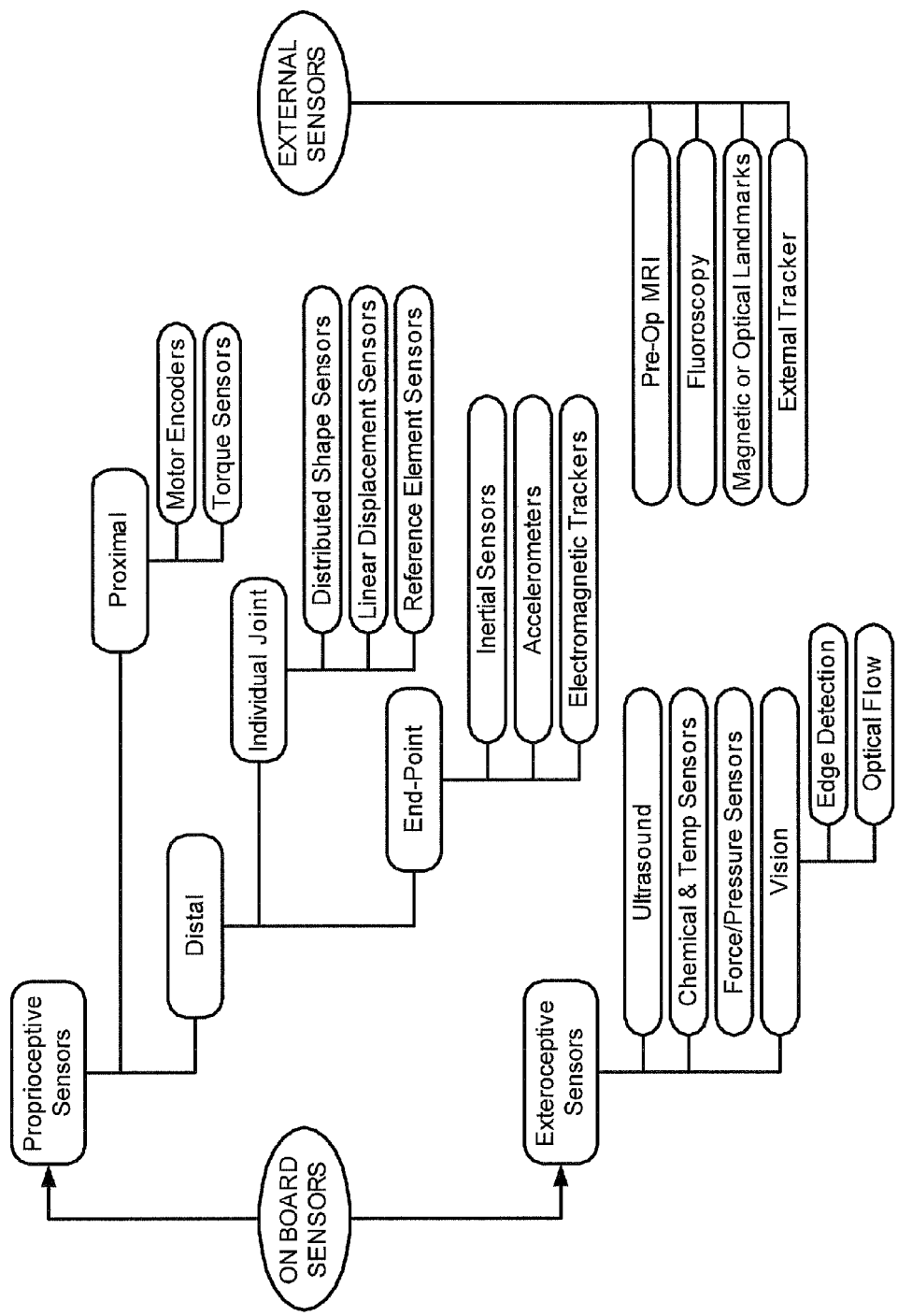
FIG. 8 illustrates a sensor classification diagram for a medical robotic system utilizing aspects of the present invention.

FIG. 8 illustrates, as an example, a sensor classification diagram for the medical robotic system 100. On board sensors include proprioceptive and exteroceptive sensors that are includable in the robotic medical system 100, whereas external sensors such as Magnetic Resonance Imaging (MRI) scanners, fluoroscopes, magnetic and optical landmark detectors, and external trackers are generally not included as part of the robotic medical system 100 but provide additional information for the surgeon.

The proprioceptive sensors are primarily used in the control system 500. In particular, proximal sensors are primarily usable as the encoders 524, 534 in the control system 500, such as motor encoders and torque sensors for the actuators 523, 533. Distal end-point sensors are primarily usable as the end-point sensor 551 in the control system 500, such as end-point mounted inertial sensors, accelerometers, and electromagnetic trackers. Micro Electro Mechanical System (MEMS) gyros and accelerometers, for example, are particularly useful for such application.

Distal individual joint sensors are primarily usable as the distal joint sensors 526, 536 in the control system 500, such as distributed shape sensors, linear displacement sensors, and reference element sensors. A Fiber-Bragg Grating sensor is one example of a distributed shape sensor, for which additional details are provided in commonly owned U.S. patent application Ser. No. 11/491,384 entitled "Robotic Surgery System including Position Sensors using Fiber Bragg Gratings," filed 20 Jul. 2006, which is incorporated herein by this reference.

Figure 10:
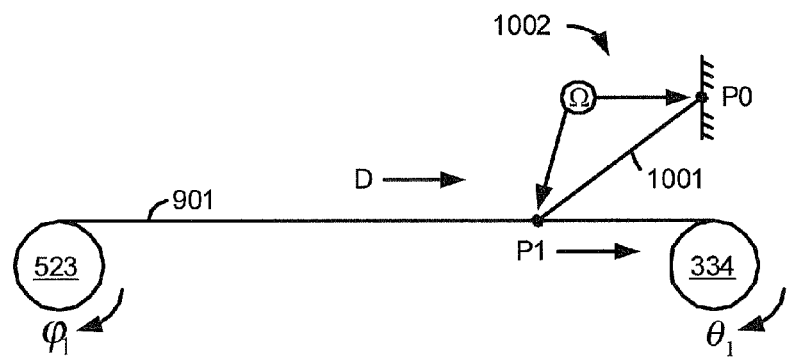
FIG. 10 illustrates a second embodiment of a linear displacement sensor for use with a control system utilizing aspects of the present invention.
Figure 11:
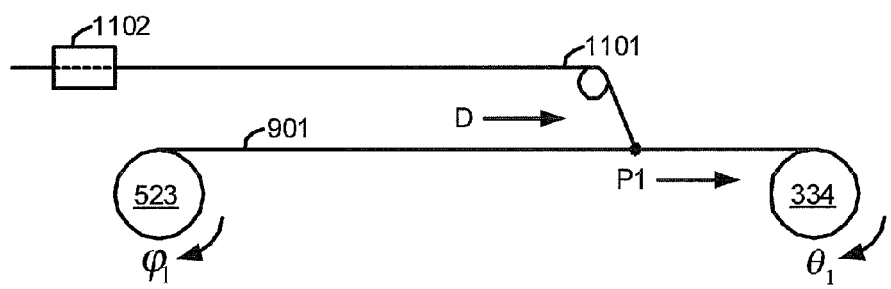
FIG. 11 illustrates a third embodiment of a linear displacement sensor for use with a control system utilizing aspects of the present invention.

Some examples of linear displacement sensors and reference element sensors are illustrated in FIGS. 9-11. In each of these examples, a cable 901 mechanically couples the actuator 523 to the distal joint 334 in a conventional manner so that a displacement $\phi_1$ of the actuator 523 causes linear movement of the cable 901 (such as in the direction "D") and a corresponding displacement $\theta_1$ of the distal joint 334. It is known that in such arrangements, friction and hysteresis of the cable 901 between the actuator 523 and the start of the cable-driven distal joint 334, due to the cable 901 going around bends and extending for long lengths, can introduce substantial uncertainties in the fine control of the articulated distal joint 334. Therefore, the inclusion of the distal joint sensor 526 in the control system 500 can provide substantial improvement over prior art control systems lacking such a sensor.

In FIG. 9, linear movement of the cable 901 is sensed by a linear displacement sensor 902 at a reference point P1 on the cable 901. The reference point P1 is selected in this case so as to be sufficiently near the distal joint 334 that movement of the cable 901 at the point P1 is a good indication of the movement of the distal joint 334. Examples of linear displacement sensors usable in this case include a Linear Voltage Differential Transformer (LVDT), a linear Hall effect sensor and a little magnet, and a slide potentiometer.

Another example of a linear displacement sensor is the sensor 1002 depicted in FIG. 10, where linear displacement of the cable 901 is estimated using the sensor 1002 by measuring the resistance $\Omega$ of a rubber part 1001 having one end attached to the cable 901 at the reference point P1 and another end attached to a fixed point P0. Still another example of measuring linear displacement is depicted in FIG. 11, where an unloaded reference cable 1101 is attached to cable 901 at the reference point P1 and its linear displacement sensed by a linear displacement sensor 1102, which may be the same type of linear displacement sensor as described in reference to FIG. 9.

Referring back to FIG. 8, exteroceptive sensors may also be used to facilitate or enhance Surgeon control of the surgical tools 338, 339 and their end effectors 322, 332, or aid the Surgeon in performing a medical procedure by providing auxiliary information of the target anatomy or surgical site. Examples of these sensors include ultrasound probes, chemical and temperature sensors, force and pressure sensors, and vision systems that perform image processing functions such as edge detection, identification of markers on the instruments, and optical flow. Vision systems with image processing may further be used as primary or supplemental end-point and/or distal bend sensors, provided the end effectors and/or distal joints are within the field of view of their cameras and the positions of their cameras are accurately known.

Although the various aspects of the present invention have been described with respect to a preferred embodiment, it will be understood that the invention is entitled to full protection within the full scope of the appended claims.

The invention claimed is:

1. In a medical robotic system, a control system for controlling an end effector of a medical device, the control system comprising:

an end effector controller configured to generate a first distal joint command using an end effector command indicative of operator manipulation of an input device and a state of the end effector;

a first distal controller configured to generate a first actuator command using the first distal joint command and a state of a first distal joint coupled to the end effector for effecting a first degree of freedom movement of the end effector; and a first proximal controller configured to close a first feedback loop around a state of a first actuator to ensure tracking of the state of the first actuator, by generating a first actuator feedback using the first actuator command and the state of the first actuator and providing the first actuator feedback to the first actuator so that the first actuator causes corresponding movement of the first distal joint and the end effector through a first cable transmission;

wherein the end effector controller is configured to generate a first feed-forward command to compensate for residual error in the first actuator feedback due to non-ideal characteristics of the first cable transmission and to provide the first feed-forward command to a summing node; and wherein the summing node is configured to sum the first actuator feedback and the first feed-forward command and to output the summed first actuator feedback and first feed-forward command to the first actuator.

2. The control system according to claim 1, further comprising an end-point sensor adapted to generate information from which the state of the end effector is determinable.

3. The control system according to claim 2, wherein the end-point sensor comprises an inertial sensor, preferably comprising a gyroscope.

4. The control system according to claim 2, wherein the inertial sensor comprises a micro electro mechanical system device.

5. The control system according to claim 2, wherein the end-point sensor comprises an accelerometer, which preferably comprises a micro electro mechanical system device.

6. The control system according to claim 2, wherein the end-point sensor employs an electromagnetic tracker.

7. The control system according to claim 1, wherein the proximal controller is configured to substantially control dynamic performance of the control system, and the distal controller is configured to substantially control steady-state performance of the control system.

8. The control system according to claim 1, further comprising a first distal joint sensor adapted to generate information from which the state of the first distal joint is determinable, and preferably wherein the first distal joint sensor comprises a distributed shape sensor or a linear displacement sensor.

9. The control system according to claim 8, wherein the linear displacement sensor is adapted to provide information from which a distance that the first cable transmission moves is determinable.

10. The control system according to claim 9, wherein the linear displacement sensor comprises a linear voltage differential transformer, or employs a Hall effect sensor and a magnet, or which comprises a slide potentiometer, or which employs a reference element coupled to the first cable transmission at a reference point so as to measure movement of the reference element as an indication of movement of the first cable transmission.

11. The control system according to claim 1, wherein the medical device comprises a single-port entry device having a plurality of surgical tools controllably extendable out of a distal end of the single-port entry device.

12. The control system according to claim 11, wherein the first cable transmission comprises a first cable, and movement of the first cable is indicative of movement of the first distal joint.

13. The control system according to claim 1, wherein the end effector controller is configured to generate a second distal joint command using the end effector command, and further comprising:

a second distal controller configured to generate a second actuator command using the second distal joint command and a state of a second distal joint coupled to the end effector for effecting a second degree of freedom movement of the end effector; and a second proximal controller configured to generate a second actuator feedback using the second actuator command and a state of a second actuator coupled to the second distal joint through a second cable transmission, and provide the second actuator feedback to the second actuator so that the second actuator causes corresponding movement of the second distal joint and the end effector.

14. The control system of claim 13, wherein the second cable transmission is characterized by non-idealities.

15. The control system according to claim 13, wherein the end effector controller is configured to generate the first distal joint command and the second distal joint command using the end effector command and a state of the end effector.

\* \* \* \* \*